United States Patent [19]

Mazomenos et al.

[11] Patent Number: 5,650,160
[45] Date of Patent: Jul. 22, 1997

[54] INCLUSION COMPLEXES OF CYCLODEXTRIN AND THEIR USE IN SLOW RELEASE FORMULATIONS FOR ATTRACTING INSECTS

[75] Inventors: Basilios Mazomenos, Halandri; Irene Moustakali-Mavridis, Papagos, both of Greece

[73] Assignee: NCSR "Demokritos", Attikis, Greece

[21] Appl. No.: 356,230
[22] PCT Filed: Jun. 17, 1993
[86] PCT No.: PCT/EP93/01536
§ 371 Date: Dec. 19, 1994
§ 102(e) Date: Dec. 19, 1994
[87] PCT Pub. No.: WO93/25076
PCT Pub. Date: Dec. 23, 1993

[30] Foreign Application Priority Data

Jun. 18, 1992 [EP] European Pat. Off. ............ 92401709

[51] Int. Cl.[6] ....................................................... A01N 25/12
[52] U.S. Cl. ...................... 424/405; 424/409; 424/413; 424/84
[58] Field of Search ........................... 424/408, 409, 424/413, 84, 405

[56] References Cited

U.S. PATENT DOCUMENTS 4,042,681  8/1977  Underhill et al. .............. 424/84

FOREIGN PATENT DOCUMENTS 0-186-146  7/1986  European Pat. Off. .
1-225644  9/1989  Japan .

OTHER PUBLICATIONS

Kondilis, P. et al, "Inclusion Complexes of Cyclodextrins with the Pheromone of the Olive Fruit Fly Dacus Oleae", *Minutes 5th Int. Symp. Cyclodexrins*, 1991, Paris, France, pp. 578–583.

Szejtli, Jozsef, "Cyclodextrin Technology", 1988, pp. 335–364.

*Primary Examiner*—Neil S. Levy
*Attorney, Agent, or Firm*—Young & Thompson

[57] ABSTRACT

Process for attracting male olive pests, particularly male *Prays oleae* or *Palpita unionalis*, wherein an appropriate amount of the following composition is used, preferably in an amount of about 10 to about 40 mg:
  an inclusion complex of a cyclodextrin and of at least one of the following compounds:
    a linear chain of 10 to 20 carbon atoms, substituted or not, saturated or unsaturated, under the acetate or aldehyde or alcohol form, provided that such chain is different from ethyl dodecanoate,
  and more particularly:
    Z-7-tetradecenal,
    E-11-hexadecenal,
    E-11-hexadecenyl acetate.

The distribution of this sex pheromone confuses the male olive pests as to the whereabouts of the females.

11 Claims, 3 Drawing Sheets

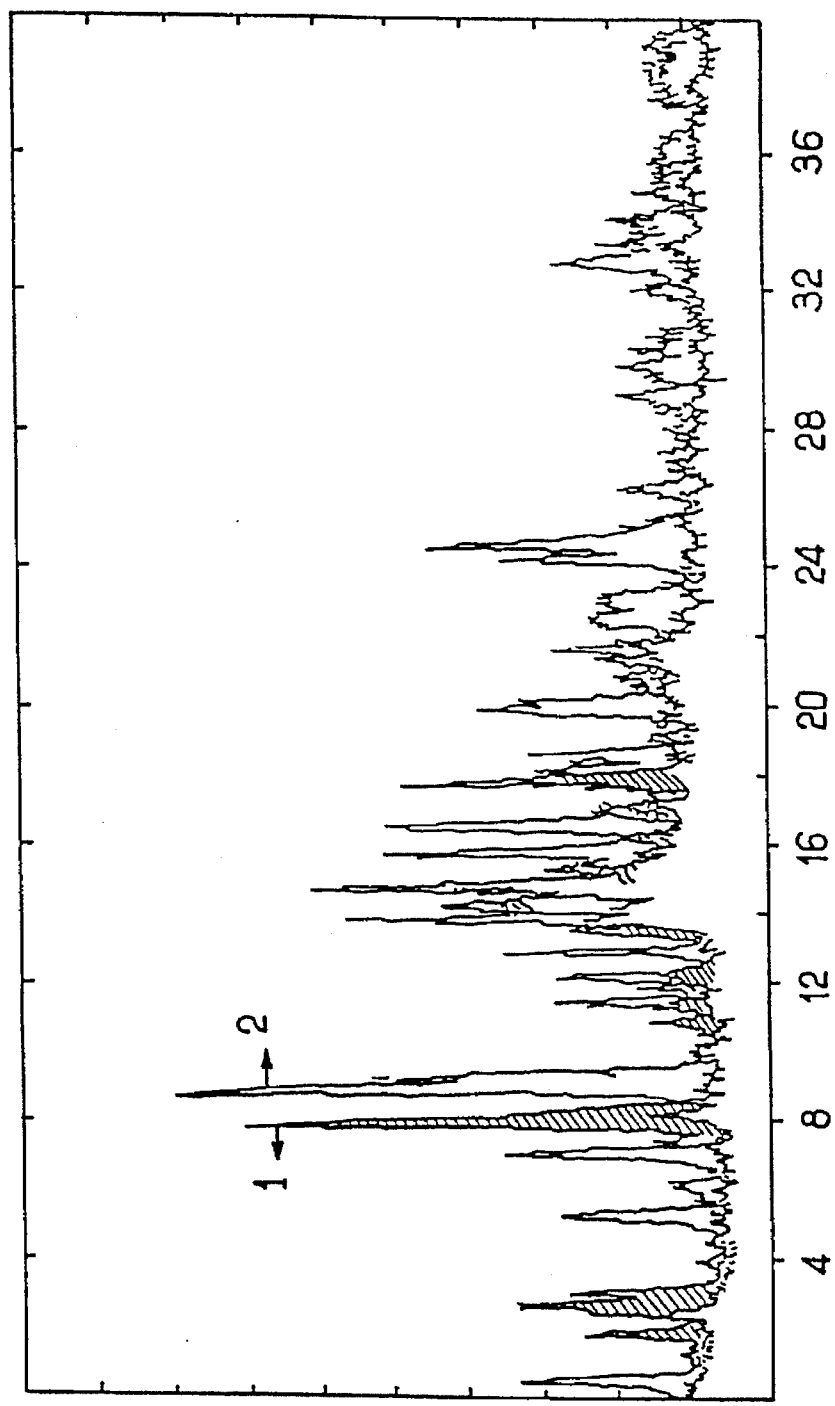
FIG_1

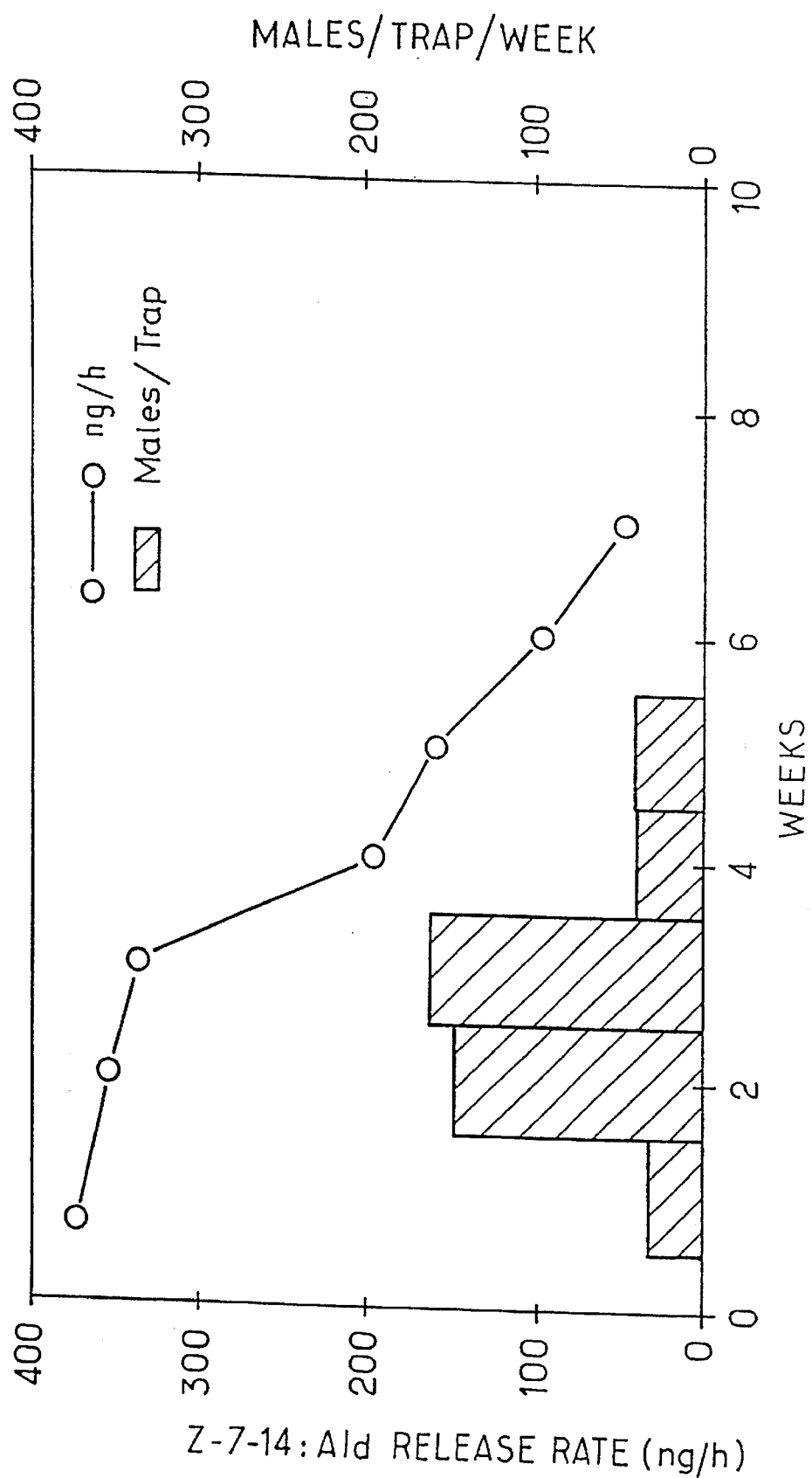
FIG_2

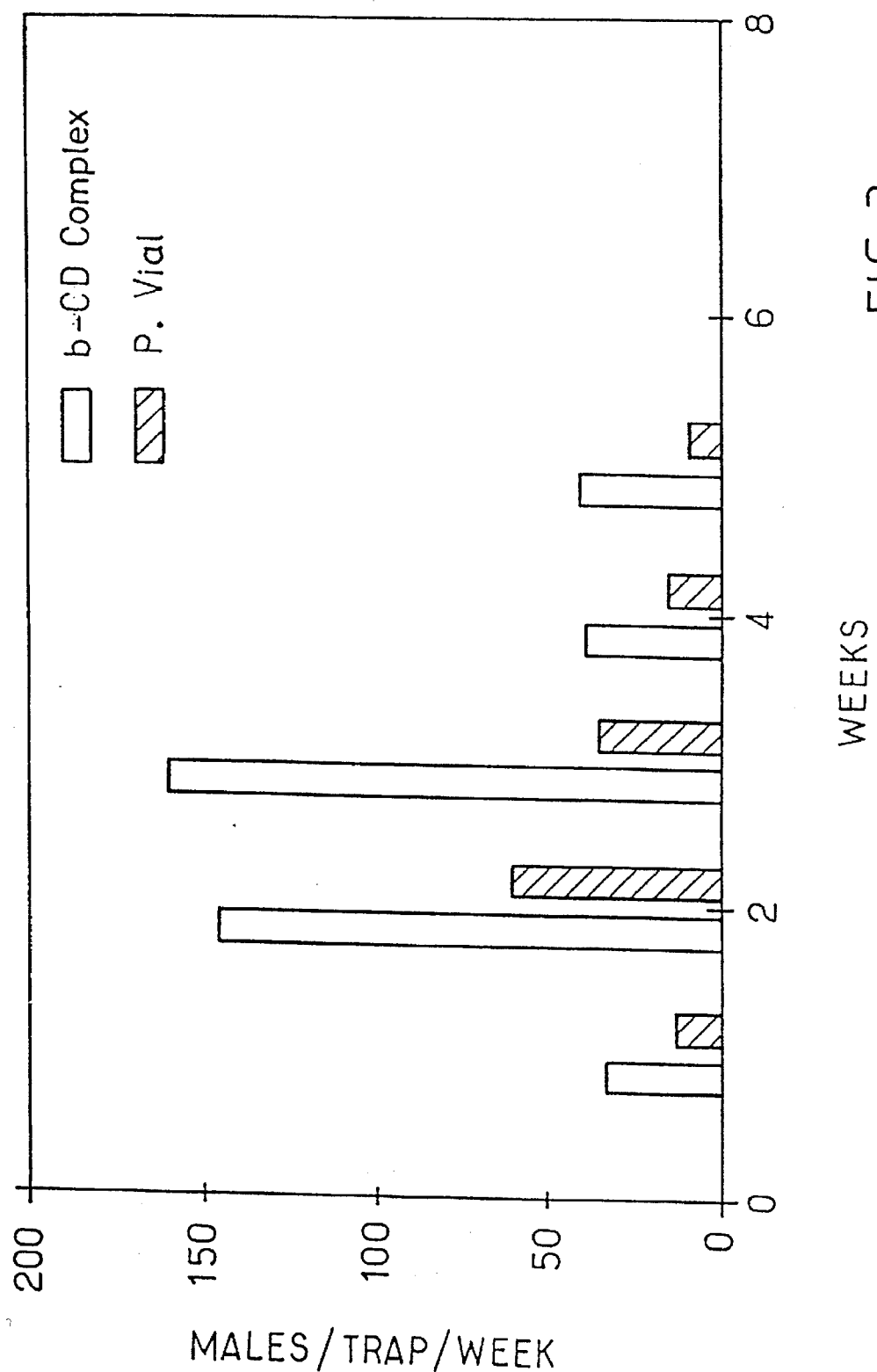
FIG_3

INCLUSION COMPLEXES OF CYCLODEXTRIN AND THEIR USE IN SLOW RELEASE FORMULATIONS FOR ATTRACTING INSECTS

The invention relates to new inclusion complexes of cyclodextrin, to a process for their preparation and to their use, particularly in slow release formulation for the treatment of Lepidopterous pests.

The olive is a tree of very special social and economical significance for the Mediterranean countries of the European Economic Community, where it occupies about 65% of the total world surface devoted to this crop and produces approximately 80% of the world production of olive oil and almost 50% of the world production of pickled olives.

Thus any development which could reduce agricultural input costs, while increasing production and quality of fruits and hence oil would be of great economic significance both within the community and in respect to its external trade.

This particularly applies for high quality olive oil (pesticide free olive oil).

Control of the Lepidopterous olive pests depends almost entirely on the use of pesticides. Their wide-spread use has already produced some serious problems in water contamination and food supplies in several locations of the olive growing countries. One of the most serious effects of using exclusively chemical insecticides for the olive pest control has been the development of pest resistance to the pesticides, the consequence of which has been the use of higher dosages which increases the environmental pollution and also affects severely the natural enemy complex with subsequent appearance of secondary pests.

*Prays oleae* is known to be a serious olive pest. The female produces and releases a sex pheromone which attracts the male. The major component of this pheromone is known and is Z-7-tetradecenal.

The jasmine moth *Palpita unionalis* [Lepidoptera: Pyralidae] is an olive pest in all the Mediterranean countries. It attacks the leaves of young olive trees and also green olives. The biology and ecology of this pest have been poorly studied. Control of this pest depends upon insecticide treatment. Extensive behavioral and chemical studies under laboratory and field conditions reveal that the females produce and release a sex pheromone which attracts the males. Up to now, the isolation and identification of the chemical components which compose the sex pheromone of the *Palpita unionalis*, had never been carried out.

The techniques which are used up to now to control the olive fruit pests, i.e. respectively *Prays oleae* and *Palpita unionalis*, are not quite adequate for the above-stated reasons, and particularly because they create water, food and environmental pollution.

Cyclodextrins and modified cyclodextrins are intermediate size compounds (MW 1000–1300), which are produced from enzymatic degradation of starch. They are composed of six, seven or eight 1,4 linked glycopyranose residues and are called, α-cyclodextrins, β-cyclodextrins, or γ-cyclodextrins (α-CD, β-CD, γ-CD) respectively. They have the shape of a truncated cone with a hydrophobic cavity at its center and its narrow and wide rims are occupied by primary and secondary hydroxyl groups, which makes its periphery hydrophilic. CDs act as hosts for a great variety of chemicals (guests) to form inclusion complexes. The guest molecules are entrapped within the cavity at least partly.

The following definitions are provided for some basic terms that are used throughout this specification.

Cyclodextrin Derivative—refers to a cyclodextrin-containing coumpound in which one or more atoms or groups of atoms are substituted at a C2, C3 or C6 hydroxyl or hydroxyl hydrogen, i.e., "modified cyclodextrins". The term cyclodextrin derivative also encompasses "linked cyclodextrins" where two or more cyclodextrins are linked together, and compounds where a useful agent such as a pharmaceutical is covalently bonded to a cyclodextrin, such that the covalent bond, when broken will yield the agent in active form. This term also includes any salt or hydrate which can be formed from the cyclodextrin derivative.

Modified Cyclodextrin—refers to a species of cyclodextrin derivatives that contains one or more atoms or groups of atoms substituted on a C2, C3 or C6 hydroxyl or hydroxyl hydrogen. The term modified cyclodextrin will not be meant to include compounds where two or more cyclodextrins are linked together, or compounds where a useful agent such as a pharmaceutical is covalently bound to a cyclodextrin. This term also includes any salt or hydrate which can be formed from the modified cyelodextrin.

Linked Cyelodextrin—refers to two or more cyclodextrins covalently linked together by one or more bridging groups. The bridging groups can link a C2, C3 or C6 position of one cyclodextrin to any one of the C2, C3, or C6 positions of the other cyclodextrin. This term includes any salt or hydrate which can be formed from the linked cyclodextrins.

Inclusion complex of cyclodextrin refers to an inclusion complex in which there are one or more associable groups or portions of a group of a cyclodextrin, or a cyclodextrin derivative which form an association with one or more associable groups or portions of a guest atom or molecule. The associable portions can include hydrophobic, Van der Waals, polar or charged groups or portions, or groups or portions capable of hydrogen bonding. This term also includes any salt or hydrate which can be formed from the inclusion-association complex.

One of the aspects of the invention is to provide the identification of the sex pheromone of *Palpita unionalis* and its use for monitoring and control.

One of the objects of the present invention is to provide inclusion complexes of cyclodextrin and the sex pheromone components of *Prays oleae* and *Palpita unionalis*.

Another object of the invention is to provide appropriate rate formulations of *Prays oleae* and *Palpita unionalis* sex pheromone.

Another object of the invention is to provide efficient formulations of *Prays oleae* and *Palpita unionalis* pheromones, which give optimum male attraction.

Another aspect of the invention is to provide a new formulation of *Prays oleae* and *Palpita unionalis* pheromone blend, enabling their release in the correct ratio and constant rate, thus highly improving their effectiveness.

Another object of the invention is to provide a controlled release system that can be applied in powder form or liquid, and which has the advantage of resorting to mechanical means for the application.

Another object of the invention is to provide protective and slow release formulation of long chain (C10–C20) pheromones.

Another aspect of the invention is to provide natural biodegradable products, which act as slow release carriers and are not detrimental to the environment.

All these aims are achieved through compositions containing an inclusion complex of a cyclodextrin and of at least one of the following compounds:

a linear chain of 10 to 20 carbon atoms, substituted or not, saturated or unsaturated, under acetate, aldehyde or alcohol form, provided that such chain is different from ethyl dodecanoate, and more particularly compounds chosen among:
- Z-7-tetradecenal (Z corresponding to cis, and 7 corresponding to the position number of the first carbon atom double-bound to the following carbon atom in this compound),
- E-11-hexadecenal (E corresponding to trans and 11 corresponding to the position number of the first carbon atom double-bound to the following carbon atom in this compound), and
- E-11-hexadecenyl acetate (E and 11 being as defined above).

By the expression "linear chain of 10 to 20 carbon atoms, substituted or not", it must be understood that it corresponds to any linear chain the framework of which is represented by these 10 to 20 carbon atoms. These 10 to 20 carbon atoms can be substituted, for example by one or several alkyl groups (such as methyl, ethyl etc . . . ), the carbon atoms of these substitution groups being not taken into account in said 10 to 20 carbon atoms representing said linear chain.

For example, a C16 linear chain according to the invention (such as hexadecenal) substituted by two methyl groups, would still be designated as C16 linear chain, whereas it comprises 18 carbon atoms.

It should also be emphasized that the three carbon atoms of the acetate, and the carbon atom of the aldehyde forms mentioned above, of the linear chain of the invention, can or cannot be taken into account in said 10 to 20 carbon atoms.

Preferably, linear chins according to the invention, are different from the following compounds: amyl cinnamic aldehyde ($C_{14}H_{20}O$), ethylene brossylate ($C_{15}H_{24}O_6$), citronellyl formate ($C_{11}H_{20}O_2$), citronellyl acetate ($C_{12}H_{22}O_2$), citral ($C_{10}H_{16}O$), citronellol ($C_{10}H_{20}O$), tetrahydrolinalool ($C_{10}H_{22}O$), and linalool ($C_{10}H_{18}O$).

Pheromones are very promising to be used as alternative methods for the control of insect pests. These chemicals can be used in traps for monitoring an insect population to measure the application of sprays or for direct control, using the mass trapping or the mating disruption techniques. Pheromones tend to be extremely volatile and they readily decompose. As a consequence formulation and dispensing mechanisms must be developed for their effective use.

According to an advantageous embodiment of the invention, the compositions contain an inclusion complex of a cyclodextrin and of Z-7-tetradecenal.

According to another advantageous embodiment of the invention, the compositions contain an inclusion complex of a cyclodextrin and of E-11-hexadecenal and/or an inclusion complex of a cyclodextrin and of E-11-hexadecenyl acetate.

In the compositions of the invention, the cyclodextrin-in is chosen from among:

β-cyclodextrin, α-cyclodextrin, γ-cyclodextrin, methylated cyclodextrin such as di-O-methyl-β-cyclodextrin, tri-O-methyl-β-cyclodextrin.

For *Palpita unionalis*, the cyclodextrin used in the compositions of the invention can be such that it is different for each inclusion complex.

In the case of *Palpita unionalis*, according to another advantageous embodiment of the invention, the same cyclodextrin is used for each of the inclusion complexes.

Complexes of α, β, and γ-cyclodextrins and the methylated cyclodextrins in various positions respectively with the two pheromone components of *Palpita unionalis* (E-11-hexadecenal and E-11-hexadecenyl acetate) and with the major component of *Prays oleae* have been prepared. The components of the pheromones form very stable inclusion complexes with the cyclodextrin. The formation of the inclusion complexes were determined by X-ray diffraction, differential scanning calorimetry and IR methods.

According to another embodiment of the invention, the compositions are such that the mount of Z-7-tetradecenal is from 2 to 20 per cent of weight of the inclusion complex with cyclodextrin.

According to another embodiment of the compositions of the invention are such that:
- the mount of E-11-hexadecenal is from 2 to 25 per cent of weight of the inclusion complex with cyclodextrin, and/or,
- the amount of E-11-hexadecenyl acetate is from 2 to 30 per cent of weight of the inclusion complex with cyclodextrin.

According to another embodiment of the invention, the compositions are such that the ratio between E-11-hexadecenal and E-11-hexadecenyl acetate is approximatively ⅗.

The compositions of the invention are advantageously in a solid state, containing, if necessary, a solid vehicle such as talc.

The release rate of the guest compound in the cyclodextrin have been monitored in the laboratory using analytical methods and under field conditions, and the longevity and stability of the pheromone complexes have been established according to NMR spectra in $D_2O$ and/or ethyl alcohol-$d_6$.

For *Prays oleae*, the release rates in powder form is of 210 ng/10 mg complex to 1000 ng/10 mg complex.

For *Palpita unionalis*, the release rates in powder form is of 150 ng/10 mg complex to 500 ng/10 mg for E-11-hexadecenyl acetate and of 200 ng/10 mg complex to 800 ng/10 mg for E-11-hexadecenal.

The invention also relates to a process for preparing a composition of the invention, said process comprising mixing the inclusion complexes, if necessary in presence of a solid vehicle, said inclusion complex being prepared by the reaction of cyclodextrin with a chain of 10 to 20 carbon atoms, under the aldehyde acetate or alcohol form.

For *Prays oleae*, said inclusion complexes can be prepared by a method comprising:
- the reaction of cyclodextrin with Z-7-tetradecenal under the conditions described in the examples,
- if necessary, purification of the inclusion complexes thus obtained.

For *Palpita unionalis*, said inclusion complexes can be prepared by a method comprising:
- the reaction of cyclodextrin with E-11-hexadecenal and/or the reaction of cyclodextrin with E-11-hexadecenyl acetate under the conditions described in the examples,
- if necessary, purification of the inclusion complexes thus obtained.

The synthesis of Z-7-tetradecenal is described in Nesbitt, B. F. Beevor, P. S. Hall, D. R. Laster, R. Sternlicht, M. and Goldenberg, S. (1977). Identification and synthesis of the female sex pheromone of the citrus flower moth *Prays citri* Biochem. 7, 355–359.

The synthesis of E-11-hexadecenal, and E-11-hexadecenyl acetate, are described in Henrick C. 1977. The synthesis of insect pheromones. Tetrahedron, Report No 34 vol. 33, 1845–1889.

The invention also relates to a process to obtain the above-mentioned pheromones from the pheromone gland of virgin females, by removing the glands with forceps and extraction in an appropriate solvent, such as methylene chloride for 20 min.

The invention also relates to a process for attracting male olive pests, particularly male or *Palpita unionalis*, wherein an appropriate amount of the composition of the invention, is used, preferably in an amount of such that it contains 0.1 to 5 mg of Z-7-tetradecenal for *Prays oleae* or 0.05 to 10 mg of E-11-hexadecenyl acetate and/or 0.02 to 3 mg of E-11-hexadecenal for *Palpita unionalis*.

The invention also relates to a process for attracting male olive pests, particularly male *Prays oleae* or *Palpita unionalis*, wherein an appropriate amount of the composition according to the invexition, is used, preferably in an amount of about 10 to about 40 mg.

For attracting male *Prays oleae* an appropriate mount of the composition comprising an inclusion complex of a cyclodextrin and Z-7-tetradecenal, such as described above, is used, preferably in an mount of 10 mg.

For attracting male olive pests, particularly *Palpita unionalis*, an appropriate amount of the composition comprising an inclusion complex of a cyclodextrin and E-11-hexadecenal and E-11-hexadecenyl acetate, such as described above, is used, preferably in an mount of 20 mg and 40 mg respectively.

The invention also relates to insecticidal compositions comprising an insecticide in combination with at least one composition of the invention.

For *Prays oleae*, the amount of insecticide used is advantageously of 10 to 20 mg for 50 mg of composition of the invention used.

For *Palpita unionalis*, the mount of insecticide used is advantageously of 10 to 20 mg for 50 mg of composition of the invention used.

The invention relates to a process for interfering with the development of insects, particularly *Prays oleae* or *Palpita unionalis* comprising the use of a composition of the invention, in an effective amount.

As to the mating disruption technique which can be developped with the use of the CD-pheromone complexes as the disruptant for said insects, it can eliminate completely the use of pesticides.

The mating disruption technique, which prevents insects from propagation, requires the permeation of the atmosphere with the sex pheromone. The sex pheromone has to be distributed in a large area in a formulation with a controlling release rate. With the sex pheromone everywhere, the sensory mechanism of the male will be saturated and therefore the male becomes confused in the treated area. Males cannot distinguish between the pheromone from the slow release formulation and that emitted from the females.

The cyclodexrin pheromone complexes can be developper in a flowable form in order to be applied by ground or air using mechanical methods.

The description will be completed by the following examples and figures which are not to be considered in a limited way.

Legend to Figures:

FIG. 1 represents X-ray powder diagrams of β-CD and inclusion complex of β-CD+Z-tetradecenal:

1. heavy lines: β-CD complex with Z-7-tetradecenal,
2. light lines: β-CD alone.

FIG. 2:

the left y-axis corresponds to the release rate of Z-7-tetradecenal (Z-7-14:Ald) expressed in ng/h for 10 mg of complex of β-CD and Z-7-tetradecenal, the right y-axis corresponds to the number of *Prays oleae* males trapped by week, the x-axis corresponds to the number of weeks.

FIG. 3:

the y-axis corresponds to the number of *Prays oleae* males trapped by week with complex of β-CD and Z-7-14:Ald (1 mg) compared to those trapped with standard polyethylene vial pheromone dispenser containing Z-7-14:Ald (1 mg), the x-axis corresponds m the number of weeks.

EXEMPLE 1

1) Preparation of the Major Pheromone Components of *Palpita Unionalis*

Insect Culture

The insects used were collected as larvae from infested olive trees, transferred in the laboratory on to *Ligustrum japonicum* leaves and were allowed to continue their development under laboratory conditions. The temperature was kept at 27°±1° C. with a 16:8 (L:D) regime and relative humidity of 60±5%. The Ligustrum leaves were replaced every other day. The pupae were maintained under similar conditions until insect emergence.

Insects were sexed at the pupal stage, three to four days after pupation. The female adults were transferred to an experimental room maintained at 25° C. with a 16:8 h light:dark regime, while males were placed in a large bioassay cage in a separate room, operated under the same conditions. A 10% sugar/water solution was provided as food for the adults.

Pheromone Collection

The pheromone was collected from the pheromone gland of two to three day-old virgin females exhibiting calling behaviour. The glands were removed with forceps and extracted in methylene chloride for 20 min. The extracts were filtered and concentrated through a 8-cm Vigreux column.

Pheromone Purification

The concentrated crude extract was first purified through a glass column packed with silica gel (0.2–0.5 mm). The components were eluted with 100 ml hexane, 200 ml 10% diethyl ether in hexane, and 250 ml diethyl ether. The activity was recovered in fraction 3.

Fraction 3 was further purified with preparative gas chromatography.

Gas Chromatographic Separation

Fraction 3 was injected on a 2m×1,8 mm (ID) column packed with 5% OV-101 on chromosorb G/HP 80–100 mesh; the column temperature was held at 120° C. for 5 min and then was programmed to 240° C. at 6° C./min. Nitrogen was used as carrier gas with a flow of 20 cm/min. Consecutive 6/min fractions were collected in liquid-nitrogen cooled glass capillaries, and each was tested for biological activity in laboratory bioassays.

Bioassays

Bioassays were conducted in a screen cage described by MAZOMENOS, B. E. 1989. Sex Pheromone Components of Corn Stalk Borer *Sesamia nonagrioides* (Lef.) Isolation, Identification, and Field Tests. Journal of Chemical Ecology 15, 1241–1247.

Usually 20–30 two to three day old males were present in the cage during the biossay. The biossays were conducted 5–6 hr after the onset of the dark phase under a uniform low level of light (ca. 5 lux.). Staples of the crude extract and the fractions obtained during the purification were pipetted onto a piece of Whatman No. 1 filter paper that was suspended about 3 cm below the top of the cage. The response of the males to the sample was observed for 10 min. The same volume of solvent on filter paper was used as control.

GC(Gas chromatography)-MS(Mass spectrum) analyses of the 2 components supported the chromatographic data.

The mass spectrum of the component 1 showed that it was a C16 mono-unsaturated aldehyde with diagnostic peaks of m/z 238 for P and 220 for P-18. The mass spectra for the 2nd established the presence of a C16 mono-unsaturated acetate (m/z 282 for P and 222 for P-60). The double-bond geometry and position are not revealed by the spectra, but the spectra were identical to that of synthetic E-11-hexadecenal (E-11-16:AId) and E-11-hexadecenyl acetate (E-11-16:Ac).

2) Preparation of Cyclodextrin—Pheromone Complexes

2a) Preparation of the Inclusion Complex of β-cyclodextrin and E-11-hexadecenal.

βcyclodextrin β-CD (1 g, $8.4 \times 10^{-4}$ moles) was dissolved in water (22 ml at 65° C.). The solution was clear when allowed to cool to room temperature. The aldehyde E-11-hexadecenal was then added (0.2 g, $8.4 \times 10^{-4}$ moles) dropwise at 55° C. A cloudy mixture appeared which was stirred at 55° C. for ½ h, and subsequently for 3 h while the suspension was allowed to achieve room temperature. It was left to stand overnight. The solid was collected by vacuum filtration, air dried, and dried further over $P_2O_5$ under vacuum (yield 83%).

2b) Preparation of the Inclusion Complex of β-cyclodextrin and E-11-hexadecenyl acetate.

β-cyclodextrin β-CD (0.8 g, $7 \times 10^{-4}$ moles) was dissolved in water (20 ml at 65° C.). The solution was clear when allowed to cool to room temperature. The acetate E-11-hexadecenyl acetate was then added (0.2 g, $7 \times 10^{-4}$ moles) dropwise at 55° C. A cloudy mixture appeared which was stirred at 55° C. for ½ h and subsequently for 3 h while the suspension was allowed to achieve room temperature. It was left to stand overnight. The solid was collected by vacuum filtration, air dried and dried further over $P_2O_5$ under vacuum (yield 72%).

2d) General Preparation of Inclusion Complexes of β-cyclodextrin and Long Chain C10–C20 Saturated and Unsaturated Alcohols, Aldehydes and Esters of Acetic Acid.

β-cyclodextrin (1 g, $8.4 \times 10^{-4}$ moles) was dissolved in water (22 ml at 65° C.). The solution was clear when allowed to cool to room temperature. The guest was then added ($8.4 \times 10^{-4}$ moles) dropwise at 55° C. and was stirred at 55° C. for ½ h and subsequently for 3–5 hours while the suspension was allowed to achieve room temperature. It was left to stand overnight. The solid was collected by vacuum filtration air dried, and further dried over $P_2O_5$ under vacuum (yield 60–90%).

3) Determination of Pheromone Release Rate

The release rate of the pheromone components from the complexes was determined by a closed looping air circulator in which 100 mg of each complex was placed for one hour at 20° C. The mount of pheromone released was absorbed on an activated charcoal trap. The trap was extracted with 15 μl of methylene chloride and the pheromone content was quantified by capillary gas chromatography. The release rate of both the aldehyde and the acetate were satisfactory and relatively constant for more than 4 weeks.

4) Field Tests

Field tests were conducted in a confidential way in 2 locations. The efficacy of different trap design, pheromone concentration and the role of each of the pheromone component and their geometrical or positional isomers and related components for male captures were evaluated.

Results of field experiments indicated that the 2 components E-11-16:Ac (E-11-hexadecenyl acetate) and E-11-16:Ald (E-11-hexadecenal) tested individually were not attractive to males. Activity was restored when the 2 components were combined. When the geometrical isomers were added male attractiveness was inhibited. Addition of E-11-hexadecenal (E-11-16:oH) and hexadecenal decrease male captures, while the addition of hexadecenyl acetate did not affect male captures (Table 1 wherein E-11-16:Ac, E-11-16:Ald, E-11-16:OH have the above said meanings; Z-11-16:Ac corresponds to Z-11-hexadecenyl acetate; Z-11-16-:Ald corresponds to Z-11-hexadecenal; Z-9-16:Ald corresponds to Z-9-hexadecenal (the double bond being in position 9); 16:Ald and 16:Ac correspond respectively to hexadecenal and hexadecenyl acetate without any double bond).

Table 1 represents the number of Male *Palpita unionalis* captured in traps baited with different combinations of synthetic sex pheromone components.

| COMPONENTS (mg) | | | | | | | | |
|---|---|---|---|---|---|---|---|---|
| E-11-16: Ac | E-11-16: Ald | E-11-16: OH | Z-11-16:Ac | Z-11-16:Ald | Z-9-16:Ald | 16: Ald | 16: AC | Total Males Trap |
| 1.0 | 0.0 | 0.0 | 0.0 | 0.0 | 0.0 | 0.0 | 0.0 | 0 |
| 0.0 | 1.0 | 0.0 | 0.0 | 0.0 | 0.0 | 0.0 | 0.0 | 0 |
| 0.7 | 0.3 | 0.0 | 0.0 | 0.0 | 0.0 | 0.0 | 0.0 | 76 |
| 0.7 | 0.3 | 0.1 | 0.0 | 0.0 | 0.0 | 0.0 | 0.0 | 15 |
| 0.5 | 0.0 | 0.0 | 0.5 | 0.0 | 0.0 | 0.0 | 0.0 | 0 |
| 0.7 | 0.0 | 0.0 | 0.0 | 0.3 | 0.0 | 0.0 | 0.0 | 0 |
| 0.7 | 0.0 | 0.0 | 0.0 | 0.0 | 0.3 | 0.0 | 0.0 | 0 |
| 0.7 | 0.3 | 0.0 | 0.0 | 0.0 | 0.0 | 0.1 | 0.0 | 45 |
| 0.7 | 0.3 | 0.0 | 0.0 | 0.0 | 0.0 | 0.0 | 0.1 | 88 |

5) Trap Design

The influence of trap design on males catches was studied in an experiment. The traps tested were a) Delta Agrisence, b) Delta plaque, c) Funnel. The pheromone was dispensed from rubber septa loaded with 1 mg of the 2 component blend. The traps were installed outside the tree canopy. Of the traps tested the Delta Agrisence and the Funnel traps were equally attractive to males 54 and 62 males were trapped respectively for the period tested. Surprisingly as no males were captured in Delta plaque traps, this seems to show that the white colour deters males.

6) Effect of Pheromone Concentration

A dose response relationship experiment was designed to determine the most effective concentration for monitoring and mass trapping. Funnel traps were baited with rubber sepia loaded with 0.1, 0.2, 0.4, 1.0 and 5.0 mg of the pheromone. Three replications were used for each concentration. The traps were cleaned once a week and the males captured were recorded.

All the concentration tested attracted males (Table 2). The number of males captured was increased in traps baited with higher concentration of pheromone. The traps baited with 5 mg of the pheromone blend attracted significantly more males than the other concentrations tested.

TABLE 2

Effect of pheromone concentration on male of *P. unionalis* captures.

| Concentration (mg) | Total Males Captured | Males/Trap/ Week* |
|---|---|---|
| 0.1 | 25 | 1.4 c |
| 0.2 | 27 | 1.5 c |
| 0.4 | 61 | 3.4 cb |
| 1.0 | 126 | 7.0 b |
| 5.0 | 295 | 16.4 a |

*Means followed by the same letter are not significantly different (Duncan's multiple range tests P = 0.05)

EXAMPLE 2

1) Preparation of the Inclusion Complex Between b-cyclodextrin and Z-7-tetradecenal Complex of β-CD with Z-7-tetradecenal. β-CD (5.4 g, $4.2 \times 10^{-3}$ moles) was dissolved in water (15 ml) at 65° C. The solution was clear when allowed to cool to room temperature. The aldehyde was then added (1 g, $4.8 \times 10^{-3}$ moles) dropwise, and a cloudy mixture appeared which was stirred at 55° C. for ½ h, and subsequently for 3 h while the suspension was allowed to achieve r.t. It was left to stand overnight. The solid was collected by vacuum filtration, air dried, and dried further over $P_2O_5$ for 3 days (yield 93%).

The formation of the inclusion complex was determined by X-ray powder diffraction pattern (see FIG. 1).

2) Release Rate

The release rate of the aldehyde was very satisfactory and relatively constant for 3 weeks which is matched with the preliminary performance of the β-CD pheromone complex baited traps as it is shown in FIG. 2. The number of insects caught in traps baited with β-CD pheromone complex was significantly higher than that caught with traps baited with standard polyethylene vial pheromone dispensers (FIG. 3).

3) Field Test

Field trials with the β-cyclodextrin-Z-7-14:ald complex were carried out in Greece. The traps used were the delta sticky traps. The traps were baited either with 10 mg of β-CD-Z-7-14:Ald or 1 mg of Z-7-14:Ald dispensed from polyethylene vials. Four replicates were used for each formulation. The traps were placed at head height on the olive trees. The distance among the traps was 200 meters. Traps were serviced twice a week and captured moth were removed and recorded. The results are shown in FIG. 3.

Formulae of Z-7-tetradecenal, E-11-hexadecenal, and E-11-hexadecenyl acetate:

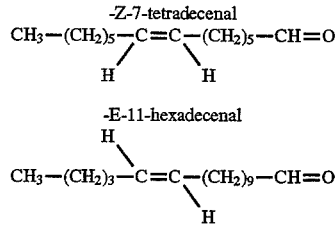

-continued
Formulae of Z-7-tetradecenal, E-11-hexadecenal, and E-11-hexadecenyl acetate:

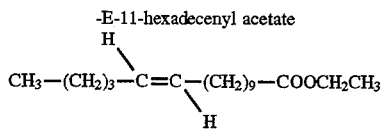

We claim:
1. Composition consisting essentially of an inclusion complex of a cyclodextrin and at least one sex pheromone component in the form of a linear chain of 10 to 20 carbon atoms, wherein said sex pheromone component is selected from the group consisting of Z-7-tetradecenal, E-11-hexadecenal, and E-11-hexadecenyl acetate.

2. The composition according to claim 1, wherein said sex pheromone component is Z-7-tetradecenal.

3. The composition according to claim 1, wherein said sex pheromone component is at least one of E-11-hexadecenal, and E-11-hexadecenyl acetate.

4. The composition according to claim 1, wherein said cyclodextrin is selected from the group consisting of β-cyclodextrin, α-cyclodextrin and γ-cyclodextrin.

5. The composition according to claim 1, wherein said cyclodextrin is a methylated cyclodextrin.

6. The composition according to claim 5, wherein said methylated cyclodextrin is di-O-methyl-β-cyclodextrin or tri-O-methyl-β-cyclodextrin.

7. The composition according to claim 2, wherein said inclusion complex comprises from 2-20% by weight of said Z-7-tetradecenal.

8. The composition according to claim 3, comprising first inclusion complexes containing E-11-hexadecenal in an amount from 2-25% by weight and second inclusion complexes comprising E-11-hexadecenyl acetate in an amount from 2-30% by weight.

9. The composition according to claim 8, wherein the ratio between E-11-hexadecenal and E-11-hexadecenyl acetate is 3:7.

10. The composition according to claim 1, further comprising a powdered excipient, said composition being in solid form.

11. Process for attracting male olive pests, comprising setting a trap in the vicinity of said pests, said trap containing from about 10 to about 40 mg of the composition according to claim 1.

* * * * *